(12) United States Patent
Bio et al.

(10) Patent No.: US 7,834,222 B2
(45) Date of Patent: Nov. 16, 2010

(54) PROCESS FOR THE PREPARATION OF BICYCLO[3.1.0]HEXANOLS

(75) Inventors: Matthew Bio, Boston, MA (US); Karel Marie Joseph Brands, Jersey City, NJ (US); Edward Cleator, Cambridge (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 340 days.

(21) Appl. No.: 11/989,885

(22) PCT Filed: Aug. 1, 2006

(86) PCT No.: PCT/GB2006/050227

§ 371 (c)(1),
(2), (4) Date: Jan. 31, 2008

(87) PCT Pub. No.: WO2007/015111

PCT Pub. Date: Feb. 8, 2007

(65) Prior Publication Data

US 2010/0099923 A1    Apr. 22, 2010

(30) Foreign Application Priority Data

Aug. 3, 2005   (GB)   .................... 0515926.4

(51) Int. Cl.
*C07C 35/27*   (2006.01)
(52) U.S. Cl. ..................................... 568/819
(58) Field of Classification Search ................. 568/819
See application file for complete search history.

(56) References Cited

FOREIGN PATENT DOCUMENTS

WO   WO 2006/114581 A1   11/2006

OTHER PUBLICATIONS

Hodgson et al., Synthesis, No. 13, pp. 2264-2266 (2005).
Hodgson et al., J. Am. Chem. Soc., vol. 126, pp. 8664-8665 (2004).
Apparu et al., Tetrahedron, vol. 34, pp. 1691-1697 (1978) (Abstract in English).

*Primary Examiner*—Sikarl A Witherspoon
(74) *Attorney, Agent, or Firm*—Dianne Pecoraro; Deeba Hussain; Catherine D. Fitch

(57) ABSTRACT

A process for the preparation of a the formula (I): which process comprises the intramolecular cyclopropanation of an epoxide of me formula (II); in the presence of 0.05 to 0.75 equivalents of a secondary amine base and at least one equivalent of an alkyl lithium base, wherein R $R^1$, $R^2$ and $R^3$ are each hydrogen or $C^{1-4}$ alkyl or $R^1$ and $R^2$ are linked to form- a $C^{3-7}$ cycloaUcyl or $C^{3-7}$ cycloalkenyl ring.

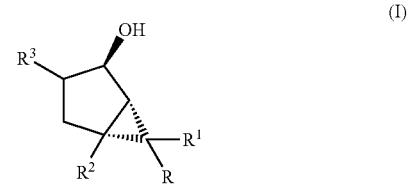

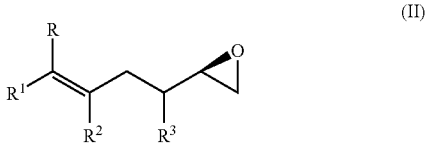

10 Claims, No Drawings

PROCESS FOR THE PREPARATION OF BICYCLO[3.1.0]HEXANOLS

This application is a §371 National Stage Application of PCT/GB2006/050227, filed on Aug. 1, 2006, which claims priority from GB Provisional Application Ser. No. 0515926.4, filed on Aug. 3, 2005.

The present invention relates to a method for preparing bicyclic alcohols containing a cyclopropyl ring.

The preparation of bicyclo[3.1.0]hexanols from unsaturated terminal epoxides is described in the Journal of the American Society 2004, 126, 8664-8665 by Hodgson et al. A variety of bicyclo[3.1.0]hexanols were prepared in yields from 69% to 81% with reaction times from 8 to 20 hours. The reaction proceeds by adding lithium 2,2,6,6-tetramethylpiperidine (LTMP) (two equivalents) dropwise to the epoxide at 0° C. in a stereospecific manner. In a further publication by Hodgson et al (Synthesis 2005, Practical Synthetic Procedures No 52), the reaction proceeds from the appropriate chlorohydrin, it being hypothesised that the lithium alkoxide of the chlorohydrin is formed which gives the epoxide in-situ; the bicyclic alcohol being formed from this. In this publication, butyl lithium (3.5 equivalents) is added to a mixture of chlorohydrin and tetramethylpiperidine (TMP) (2.5 equivalents). It is stated that using less butyl lithium or TMP was detrimental to the yield. Unfortunately, TMP is an expensive reagent.

It has now been discovered that bicyclo[3.1.0]alkanols can be prepared from unsaturated terminal epoxides using catalytic amounts of TMP and much reduced butyl lithium stoichiometries in high yield. Furthermore, lower volumes of solvent are required proportionately to carry out the reaction than described previously.

Accordingly, the present invention provides a process for the preparation of a compound of the formula (I):

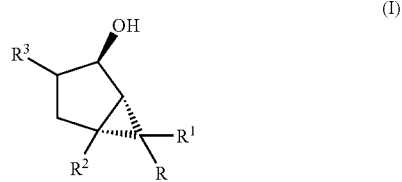

(I)

which process comprises the intramolecular cyclopropanation of an epoxide of the formula (II);

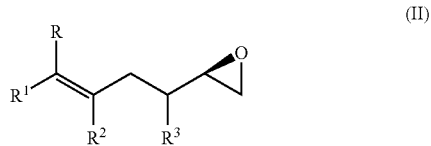

(II)

in the presence of 0.05 to 0.75 equivalents of a secondary amine base and at least one equivalent of an alkyl lithium base, wherein R, $R^1$, $R^2$ and $R^3$ are each hydrogen or $C^{1-4}$ alkyl or $R^1$ and $R^2$ are linked to form a $C^{3-7}$ cycloalkyl or $C^{3-7}$ cycloalkenyl ring. Suitably the secondary amine base is diisopropyl amine or tetramethylpiperidine and preferably it is tetramethylpiperidine. The alkyl lithium base is conveniently butyllithium present in more than 1 equivalent. Suitably 1.0 to 1.25 equivalents, and preferably about 1.1 equivalents of butyllithium is present. The alkyl lithium base serves to deprotonate the secondary amine base, which proceeds to deprotonate the epoxide and induce cyclization. It is therefore preferable to add the alkyl lithium slowly so that the concentration of alkyl lithium in the presence of epoxide is minimised.

Suitably, R, $R^1$, $R^2$ and $R^3$ are each independently selected from hydrogen, methyl, ethyl and isopropyl and preferably each is hydrogen.

Suitably, 0.1 to 0.5 equivalents TMP are present. In one embodiment of the present invention, 0.5 equivalents TMP are present.

Normally, the reaction is carried out in a suitable non-reactive solvent, for example an ether such as tert-butylmethyl ether (5 to 50 volumes and conveniently 10 volumes), If desired, the epoxide may be formed in-situ.

In one embodiment of the present invention, the epoxide and TMP (0.5 equivalents) are mixed in a suitable solvent, for example an ethereal solvent such as tert-butylmethyl ether (5 to 50 volumes and conveniently 10 volumes), and the mixture cooled, conveniently to −20° C. to 5° C. and suitably −5° C. to 0° C. n-Butyllithium or n-hexyllithium (1.1 equivalents) is then added maintaining the depressed temperature, preferably 0° C. or below, and maintaining the reaction mixture at this temperature until reaction is complete.

Other suitable solvents for carrying out the reaction include other ethereal solvents such as diethyl ether and aliphatic hydrocarbon solvents such as heptane. Another suitable ethereal solvent is THF.

When used herein, "equivalents" refers to the number of moles of TMP used per mole of epoxide and "volumes" refers to the amount of solvent in litres used per kilogram of epoxide.

The reaction mixture is suitably quenched by adding dilute acid, for example a dilute mineral acid such as dilute hydrochloric acid, whilst maintaining the depressed temperature, preferably 0° C. or below. The pH is suitably maintained at between 4.5 and 7.0 during the quenching reaction. The organic phase is then collected and may be washed, for example with further dilute acid. Alternatively the reaction may be quenched with an organic acid such as acetic acid, in which case the acetate salt of the TMP can be filtered off and the filtrate used in further processing. The total yield of bicyclic alcohol may be increased by extracting the aqueous phase with a suitable organic solvent, conveniently the solvent used for the reaction, eg an ether such as tert-butylmethyl ether. Optionally, the organic phase can be combined with the organic extracts.

The following example serves to illustrate the process of present invention:

EXAMPLE 1

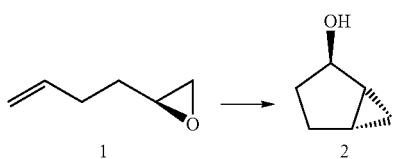

R-(+)-Epoxide (1) (100 g, 1.019 mol) was dissolved in dry tert-butylmethyl ether MTBE (1 L). To this solution was added 2,2,6,6-tetramethylpiperidine (71.96 g, 0.509 mol) and the reaction mixture was cooled to between −5 and 0° C.

n-HexLi (2.3 M in hexanes, 487 mL, 1.121 mol) was added over 4 hours keeping the temperature below 0° C. The resulting solution was aged at this temperature until all the starting epoxide was consumed according to GC analysis (approximately 4 hours). The reaction mixture was carefully quenched by the addition of 3N HCl (543 mL) whilst maintaining the internal temperature<0° C. The aqueous phase was separated and the organic phase washed with 3N HCl (170 mL). The combined aqueous layers were back extracted with MTBE (500 mL and 250 mL). The combined organic extracts were then concentrated to a total volume of approximately 450 mL. The final organic layer contained 84.8 g of 2 (86% yield) according to GC analysis.

EXAMPLE 2

R-(+)-Epoxide (1) (1 g, 0.01 mol) was dissolved in dry tert-butylmethyl ether MTBE (10 ml). To this solution was added 2,2,6,6-tetramethylpiperidine (0.72 g, 0.005 mol) and the reaction mixture was cooled to between −5 and 0° C. n-HexLi (2.5 M in hexanes, 8.16 mL, 0.002 mol) was added over 4 hours keeping the temperature below 0° C. The resulting solution was aged at this temperature until all the starting epoxide was consumed according to GC analysis (approximately 4 hours). The reaction mixture was carefully quenched by the addition of 3N HCl (543 mL) whilst maintaining the internal temperature<0° C. The aqueous phase was separated and the organic phase washed with 3N HCl (1.7 mL). The combined aqueous layers were back extracted with MTBE (5 mL and 2.5 mL). The combined organic extracts were then concentrated to a total volume of approximately 4.5 mL. The final organic layer contained 0.97 g of 2 (97% yield) according to GC analysis.

We claim:

1. A process for the preparation of a compound of the formula (I):

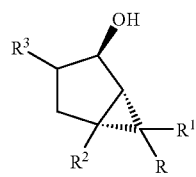

(I)

which process comprises the intramolecular cyclopropanation of an epoxide of the formula (II);

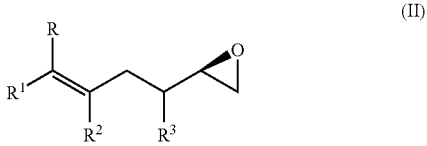

(II)

in the presence of 0.05 to 0.75 equivalents of a secondary amine base and at least one equivalent of an alkyl lithium base, wherein R, $R^1$, $R^2$ and $R^3$ are each hydrogen or $C^{1-4}$ alkyl or $R^1$ and $R^2$ are linked to form a $C^{3-7}$ cycloalkyl or $C^{3-7}$ cycloalkenyl ring.

2. A process according to claim 1, wherein the secondary amine base is diisopropyl amine or tetramethylpiperidine.

3. A process according to claim 2, wherein the secondary amine base is tetramethylpiperidine.

4. A process according to claim 3, wherein 0.1 to 0.5 equivalents of tetramethylpiperidine is present.

5. A process according to claim 1, wherein the alkyl lithium base is butyllithium.

6. A process according to claim 5, wherein more than 1 equivalent of butyllithium is present.

7. A process according to claim 1, wherein the alkyl lithium is slowly added so that the concentration of alkyl lithium in the presence of epoxide is minimised.

8. A process according to claim 1, wherein R, $R^1$, $R^2$ and $R^3$ are each independently selected from hydrogen, methyl, ethyl and isopropyl.

9. A process according to claim 1 wherein the epoxide and tetramethylpiperidine are firstly mixed in a suitable solvent, then the mixture is cooled and n-Butyllithium or n-hexyllithium added whilst maintaining the depressed temperature until the reaction is complete.

10. A process according to claim 1, wherein the reaction is carried out in an ethereal solvent.

* * * * *